(12) United States Patent
Anderson

(10) Patent No.: US 6,190,672 B1
(45) Date of Patent: *Feb. 20, 2001

(54) PARAFFIN BATH MIXTURE REFILL AND METHODS OF MANUFACTURE AND USE THEREFOR

(75) Inventor: Patrick J. Anderson, Stillwater, MN (US)

(73) Assignee: WR Medical Electronics Co., Stillwater, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/999,161

(22) Filed: Dec. 30, 1997

Related U.S. Application Data

(60) Provisional application No. 60/034,386, filed on Dec. 30, 1996, now abandoned.

(51) Int. Cl.[7] ............................. A61K 9/00; A61B 17/06; B65D 83/04; B65D 1/34
(52) U.S. Cl. ......................... 424/400; 206/538; 206/438; 206/561
(58) Field of Search ..................................... 424/400, 401, 424/61; 514/886, 887; 206/538, 438, 561

(56) References Cited

PUBLICATIONS

Advertisement—Amber, Paraffin Refill, Jan. 1991.*
Advertisement—Depileve, White unscented paraffin.*
Advertisement—Grimm Scientific Ind., PARAlin paraffin refills.*
Advertisement—Talcott Laboratories, Paraffin Chips.*
Therabath® Paraffin Heat Therapy System, assorted product literature (dated Jun. 1995 –Nov. 1995), including Therabath® Paraffin EZ Cubes™.
Para–Salon (Bristol, PA), "Nails Magazine," Advertisement (3 Sheets), (May 31, 1988).
Amber Skin Care Products (Cleveland, OH), Advertisement (4 Sheets), (Jan. 31, 1989).
Amber (Cleveland, OH), Advertisement (3 Sheets), (Jan. 31, 1991).
Para–Salon, Gigi Laboratories (Los Angeles, CA), Advertisement (1 Sheet), 1991.
Avinal (No Address Given), Advertisement (1 Sheet), Undated.
Depiléve (No Address Given), Advertisement (1 Sheet), Undated.
Gena Laboratories (Duncanville, TX), Advertisement (3 Sheets), Undated.

(List continued on next page.)

Primary Examiner—Thurman K. Page
Assistant Examiner—Brian K. Seidleck
(74) Attorney, Agent, or Firm—Fredrikson & Byron, P.A.

(57) ABSTRACT

A paraffin refill or package system or article wherein the paraffin mixture is provided in a large total volume which has preselected portions or sub-volumes which are defined by a divider structure. The sub-volumes or portions are preferably cube shaped. In use, a single carton containing the paraffin refill or system is opened. One or more portions or cubes of the system are added to the bath apparatus reservoir and heated. The user then observes the resultant liquefied mix to determine whether additional portions of the system are necessary. Any remaining portions of the system are saved in the carton. The paraffin refill or package system is made by a method basically comprising the steps of placing a divider structure in a molding container, adding a mixture of melted paraffin wax and liquid mineral oil to the container; cooling the mixture or permitting the mixture to cool to a predetermined temperature so that it solidifies; and placing the solidified mixture and divider structure in a package or a paraffin bath.

14 Claims, 2 Drawing Sheets

OTHER PUBLICATIONS

Grimm Scientific Ind (Marietta, OH), Advertisement (1 Sheet), Undated.
Light Concept Nails (No Address Given), Advertisement (1 Sheet), Undated.
Talcott Laboratories Inc. (McDonald, PA), Advertisement (4 Sheets), Undated.
Dickson, Thermo–Electric Co. (Cleveland, OH), Advertisement (2 Sheets), Undated.

Waxwel, Fabrication Enterprises Incorporated (Irvington, NY), Advertisement (2 Sheets), Undated.

* cited by examiner

_US 6,190,672 B1_

PARAFFIN BATH MIXTURE REFILL AND METHODS OF MANUFACTURE AND USE THEREFOR

CROSS-REFERENCE TO RELATED APPLICATIONS, IF ANY

This application claims the benefit under 35 U.S.C. §119 (e) of provisional application Serial No. 60/034,386, filed Dec. 30, 1996, now abandoned which is hereby incorporated by reference.

BACKGROUND OF THE INVENTION

1. Field of the Invention

The present invention relates, generally, to cosmetological apparatus and methods and medical devices and methods. More particularly, the invention relates to paraffin skin moisturizing and/or pain relief apparatus, articles and methods.

2. Background Information

The state of the art includes various devices and methods related to paraffin skin moisturizing and pain relief apparatus and articles. WR Medical Electronics Co. of Stillwater, Minn. USA, applicant's assignee, manufactures and sells the THERABATH II® portable paraffin therapy bath. The paraffin bath or spa comprises a heated tank which holds a paraffin mixture heated to a predetermined temperature and liquefied. The liquefied paraffin mixture is used in, inter alia, manicures, pedicures and facials for moisturizing, and for heat therapy for pain relief or inflammation reduction in for example patients who have chronic joint diseases such as arthritis, chronic or acute orthopedic injuries or conditions such as inflammation stiffness or muscle spasm, sports injuries, or other medical conditions.

The paraffin is commonly supplied to the bath in a solid or semi-solid form article which is a mixture of refined paraffin wax and mineral oil. Other elements may be added such lanolin, vitamins, fragrance or the like. An example of a paraffin mixture is THERAFFIN® paraffin mixture sold by WR Medical Electronics Co. The solid mixture typically comes in the form of a relatively large block, brick, cartridge or tub, typically approximately six (6) to twenty-two (22) pounds in weight. An example of this type of refill is the ONESTEP™ Theraffin Refill sold by WR Medical Electronics Co. It is necessary to cut or slice the large block into portions of a size which will fit into a bath apparatus. Another refill system comprises individually packaged sticks of approximately one (1) pound each, for example the THERAFFIN® wax stick sold by WR Medical Electronics Co. Other systems include trays or pouches in smaller sizes ranging from one half (½) to four (4) pounds. Finally, the paraffin may come in the form of chips, beads or another solid particulate form in a bag or container, which is mixed with liquid oil directly in the bath.

Prior art paraffin mixture refill articles, and their methods of manufacture and use are believed to have significant limitations and shortcomings. For example, blocks and the like must be sliced or cut to size prior to insertion, thus necessitating the provision of and use of a separate tool and requiring extra time for bath set-up. Also, the use of these larger portions necessitate the use of a secondary paraffin refill system consisting of smaller units or chips to add small amounts of paraffin to maintain a virgin paraffin level when the heater unit is in constant use. Sticks typically come in separate packages which must be cut open and discarded, resulting in additional time spent and waste generated. Pouches and trays tend to flake when peeled from containers. And, chips must be poured and have oil added thereto, which is typically quite messy.

Applicant's invention provides an improved paraffin package system or refill article for a paraffin bath which clearly overcomes the limitations and shortcomings of the prior art. Applicant's invention also provides a method of manufacturing the refill article and a method of using the refill article with a paraffin bath.

BRIEF SUMMARY OF THE INVENTION

The present invention provides an improved paraffin refill or package system or article wherein the paraffin mixture is provided in a large total volume which has preselected portions or sub-volumes. The sub-volumes or portions are preferably cube shaped.

In use, a single carton containing the paraffin refill or system is opened. One or more portions or cubes of the system are added to the bath apparatus reservoir and heated. The user then observes the resultant liquefied mix to determine whether additional portions of the system are necessary. Any remaining portions of the system are saved in the carton.

The paraffin refill or package system is made by a method basically comprising the steps of:

(a) placing a divider structure in a molding container, (b) adding a mixture of melted paraffin wax and liquid mineral oil to the container, (c) cooling the mixture or permitting the mixture to cool to a predetermined temperature so that it solidifies, and (d) placing the solidified mixture and divider structure in a package or a paraffin bath.

Significant features of the invention include:

(1) The article of this invention is preblended with optimized proportions of highly refined, medical components, with no need to mix.

(2) Compared to blocks, the article requires no tools and is simpler and faster to use.

(3) Compared to sticks, the article does not require cutting open packages and generates less packaging waste.

(4) Compared to chips, no mixing of paraffin and liquid mineral oil is required, saving time and creating no mess.

The features, benefits and objects of this invention will become clear to those skilled in the art by reference to the following description, claims and drawings.

DETAILED DESCRIPTION

Figure 1:
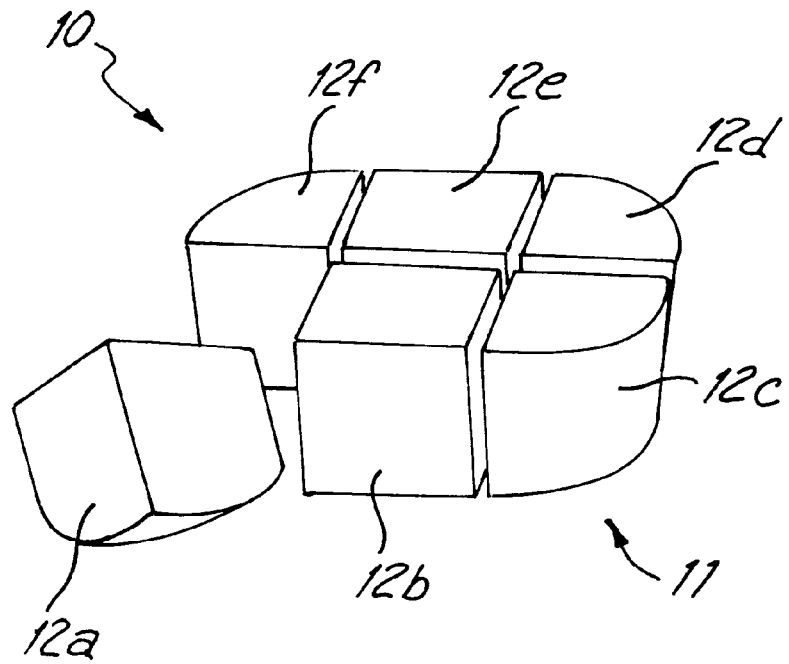
FIG. 1 is a perspective view of the paraffin refill article of the present invention.
Figure 2:
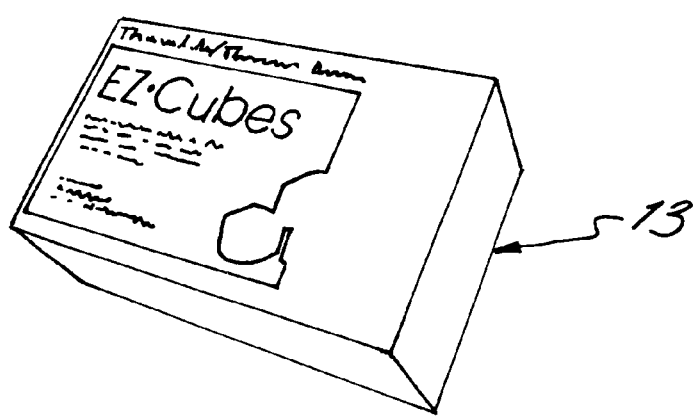
FIG. 2 illustrates the carton for housing the article.
Figure 3:
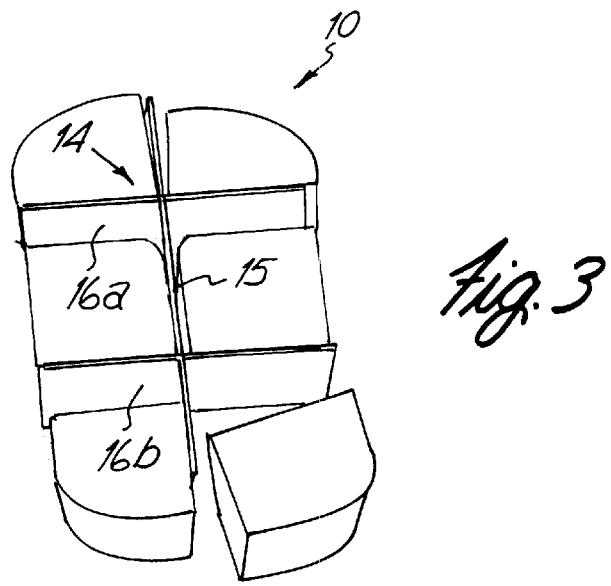
FIG. 3 illustrates the article including its divider.

Referring to FIGS. 1–3, an example of the preferred embodiment of the present invention is illustrated.

The present invention provides an improved paraffin refill article 10 wherein a substantially solid paraffin mixture is provided in a body 11 of predetermined total volume which has preselected portions 12a–f of approximately equivalent sub-volumes, and which are defined and separated by a divider structure 14. The divider structure preferably consists of a rectilinear longitudinal member 15 of a predetermined length and height and two lateral member 16a and 16b of an equivalent length and a height equivalent to that of the longitudinal portion. Preferably six portions 12 are provided, although the number of portions may be increased or decreased. The weight of total body 11 is preferably approximately six pounds and is tub shaped with flat top and bottom ends, and flat sides with rounded edges. The portions 12 are preferably one pound each in weight and are generally cube shaped. The size, weight and shape of the article 10 and portions 12 may be varied. The article 10 is packaged in a single carton 13, constructed of paperboard or a similar material. Alternatively, the entire article 10 may be placed directly in a paraffin bath device (not shown) for example by the bath device manufacturer as an initial supply.

Figure 4:
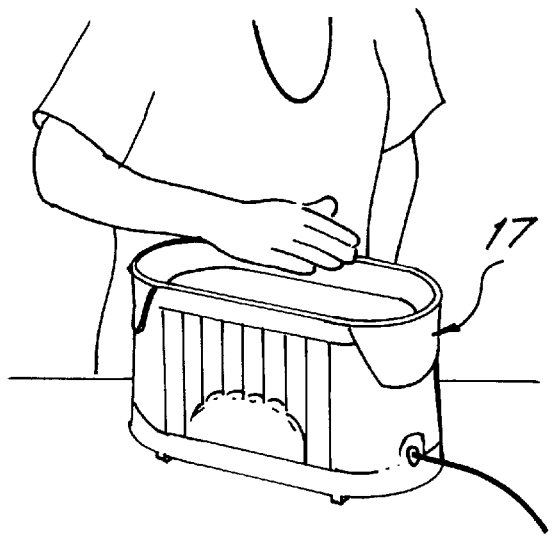
FIG. 4 illustrates an exemplary paraffin therapy bath with which the article of the present invention is used.
Figure 5:
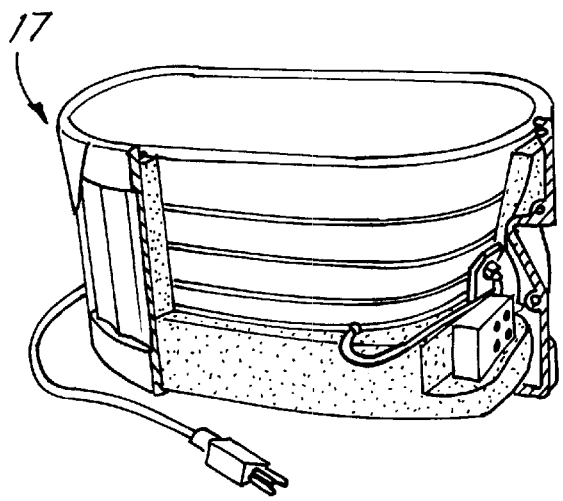
FIG. 5 illustrates the bath of FIG. 4 with a portion cut away to show interior components thereof

In use, a single carton containing the paraffin refill or system 10 is opened. One or more portions or cubes 12 are removed from the system 10 by simply and easily lifting the portion or portions 12 away from the divider 14. The portion or portions 12 are then added to a bath apparatus reservoir and heated for approximately 2 to 4 hours. An exemplary bath apparatus 17 is shown in FIGS. 4 and 5 and further disclosed in the published THERABATH II Portable Paraffin Therapy Bath Product Information brochure (Form No. 2044 rev. May. 15, 1996) of WR Medical Electronics Co. which is hereby incorporated by reference. The user then observes the resultant liquefied mix to determine whether additional portions of the system are necessary to achieve a proper fill level in the bath apparatus 17 reservoir. Any remaining portions of the article are saved in the carton.

The paraffin refill or package system 10 is made by a method basically comprising the steps of:

(a) placing a divider structure 14 in a molding container, (b) adding a mixture of melted or liquefied paraffin wax and liquid mineral oil to the container, (c) cooling the mixture or permitting the mixture to cool to a predetermined temperature so that it solidifies, and (d) placing the solidified mixture and divider structure 14 in a package 13 or a paraffin bath apparatus 17.

The mixture may also contain a fragrance, skin softeners such as lanolin, one or more vitamins, and the like.

The divider 14 is preferably constructed of a paper material and includes a series of cubical forming right angled members 15 and 16.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

The invention claimed is:

1. A paraffin refill article for a paraffin bath comprising a paraffin mixture body which has a plurality of separate cube-shaped portions which are separated by a removable divider structure, wherein the refill article, including the divider structure, is packaged in a single carton, and wherein the paraffin mixture body comprises paraffin and mineral oil.

2. The article of claim 1, wherein said paraffin mixture body further comprises at least one constituent selected from the group of constituents consisting of a fragrance constituent, a skin softening constituent, and a vitamin containing constituent.

3. The article of claim 1, wherein the article has a total weight of approximately six pounds and wherein there are six substantially equivalent portions, by weight, each weighing approximately one pound.

4. The article of claim 1, wherein the divider structure is constructed of paper.

5. The article of claim 1, wherein the divider structure comprises a longitudinal member and at least one lateral portion oriented substantially at a right angle to the longitudinal member.

6. A readily separable paraffin refill system for use with a heated, therapeutic paraffin bath to provide easy adjustment of the amount of melted paraffin mixture in the bath, comprising:

(a) a solid paraffin mixture body which has a plurality of portions, the paraffin mixture body comprising paraffin and mineral oil;

(b) a divider structure constructed of paper and separating and defining the portions of the body, the divider structure comprising a longitudinal member and at least one lateral portion oriented substantially at a right angle to the longitudinal member; and (c) an outer package surrounding the article.

7. A method of using paraffin refill article for a paraffin bath comprising a paraffin mixture body, comprising paraffin and mineral oil, which has a plurality of separate portions, divided by a divider structure, all disposed in a single carton, comprising the steps of:

(a) opening the carton containing the paraffin refill article, (b) removing at least one portion and adding said at least one portion to the bath, (c) heating the bath and observing the resultant liquefied mix to determine whether an additional portion or portion wanted, and (d) placing any remaining portions of the article body in a carton.

8. The method of claim 7, wherein the article used further comprises:

a divider structure constructed of paper and separating and defining the portions of the body, the divider structure comprising a longitudinal member and at least one lateral portion oriented substantially at a right angle to the longitudinal member; and an outer carton surrounding the article.

9. A method of manufacturing a paraffin refill article for a paraffin bath comprising a paraffin mixture body which has a plurality of separate portions, comprising the steps of:

(a) placing a divider structure in a molding container, (b) adding a mixture of melted paraffin wax and liquid mineral oil to the container, (c) cooling the mixture or permitting the mixture to cool to a predetermined temperature so that it solidifies, and (d) placing the solidified mixture and divider structure in a package or a paraffin bath.

10. The method of claim 9, wherein the article constructed further comprises:

(a) a solid paraffin mixture body which has a plurality of portions, the paraffin mixture body comprising paraffin and mineral oil; and (b) a divider structure constructed of paper and separating and defining the portions of the body, the divider structure comprising a longitudinal member and at least one lateral portion oriented substantially at a right angle to the longitudinal member.

11. An article according to claim 1 wherein the divider structure comprises a rectilinear longitudinal member and one or more lateral members of equivalent length and at substantially right angles to the longitudinal member, the lateral members being of equivalent height to the longitudinal member.

12. A system according to claim 6 wherein the divider structure comprises a rectilinear longitudinal member and one or more lateral members of equivalent length and at substantially right angles to the longitudinal member, the lateral members being of equivalent height to the longitudinal member.

13. A method according to claim 7 wherein the divider structure comprises a rectilinear longitudinal member and one or more lateral members of equivalent length and at substantially right angles to the longitudinal member, the lateral members being of equivalent height to the longitudinal member.

14. A method according to claim 10 wherein the divider structure comprises a rectilinear longitudinal member and one or more lateral members of equivalent length and at substantially right angles to the longitudinal member, the lateral members being of equivalent height to the longitudinal member.

* * * * *